United States Patent [19]
Margolin

[11] Patent Number: 5,168,725
[45] Date of Patent: Dec. 8, 1992

[54] CRYOGENIC STORAGE OF PERISHABLE FLUIDS

[75] Inventor: Ely Margolin, Coral Springs, Fla.

[73] Assignee: National Health Guard, Inc., Fort Lauderdale, Fla.

[21] Appl. No.: 572,907

[22] Filed: Aug. 24, 1990

[51] Int. Cl.⁵ .................. F17C 13/00; F25B 21/00
[52] U.S. Cl. ................... 62/457.9; 62/78; 62/440; 62/446
[58] Field of Search ............ 62/78, 440, 457.9, 446, 62/388, 306

[56] References Cited

U.S. PATENT DOCUMENTS

| | | |
|---|---|---|
| 3,006,707 | 10/1961 | Rossi ..................... 62/446 X |
| 3,163,994 | 1/1965 | Haumann . |
| 3,303,667 | 2/1967 | Perkins . |
| 3,916,640 | 11/1975 | Rasovich . |
| 3,952,536 | 4/1976 | Faust . |
| 4,665,713 | 5/1987 | Delatte . |
| 4,898,294 | 2/1990 | Jennings ................ 62/457.9 X |
| 4,928,502 | 5/1990 | Kumada et al. ............ 62/78 X |
| 4,958,498 | 9/1990 | Brothers ................. 62/78 X |
| 4,976,112 | 12/1990 | Roberts et al. ........... 62/457.9 X |

Primary Examiner—Lloyd L. King
Attorney, Agent, or Firm—Stanger, Michaelson, Spivak & Wallace

[57] ABSTRACT

A cryogenic storage system affords dense packing and easy access to individually identified storage packets of frozen fluid, such as blood, by storing the storage packets in an array of individually identified vertically movable racks, each containing a stack of individually identified storage packets, within a grid beneath the opening of a cryogenic tank. Preferably, the storage packets are substantially flat and the racks hold the storage packets in vertical edge-to-edge relationship.

10 Claims, 7 Drawing Sheets

FIG. 6
FIG. 7
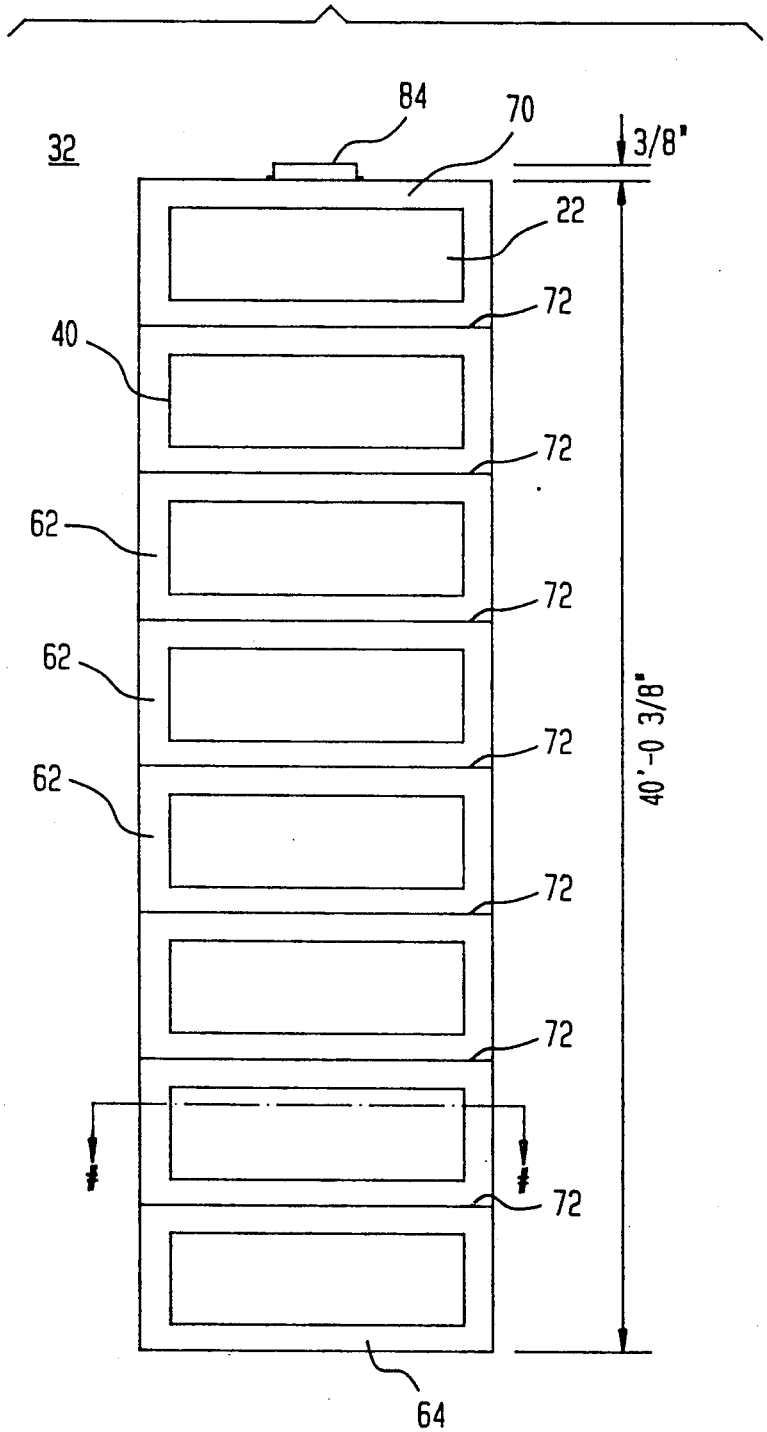
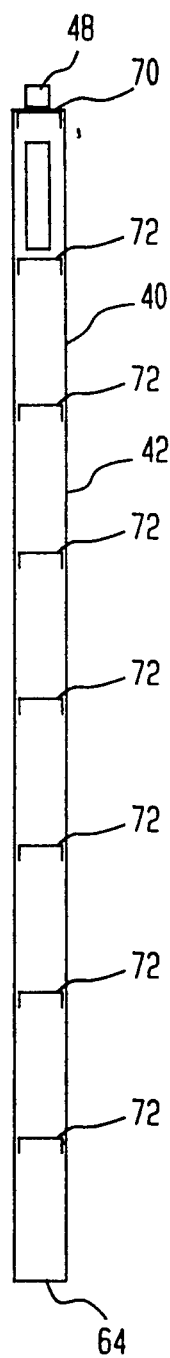

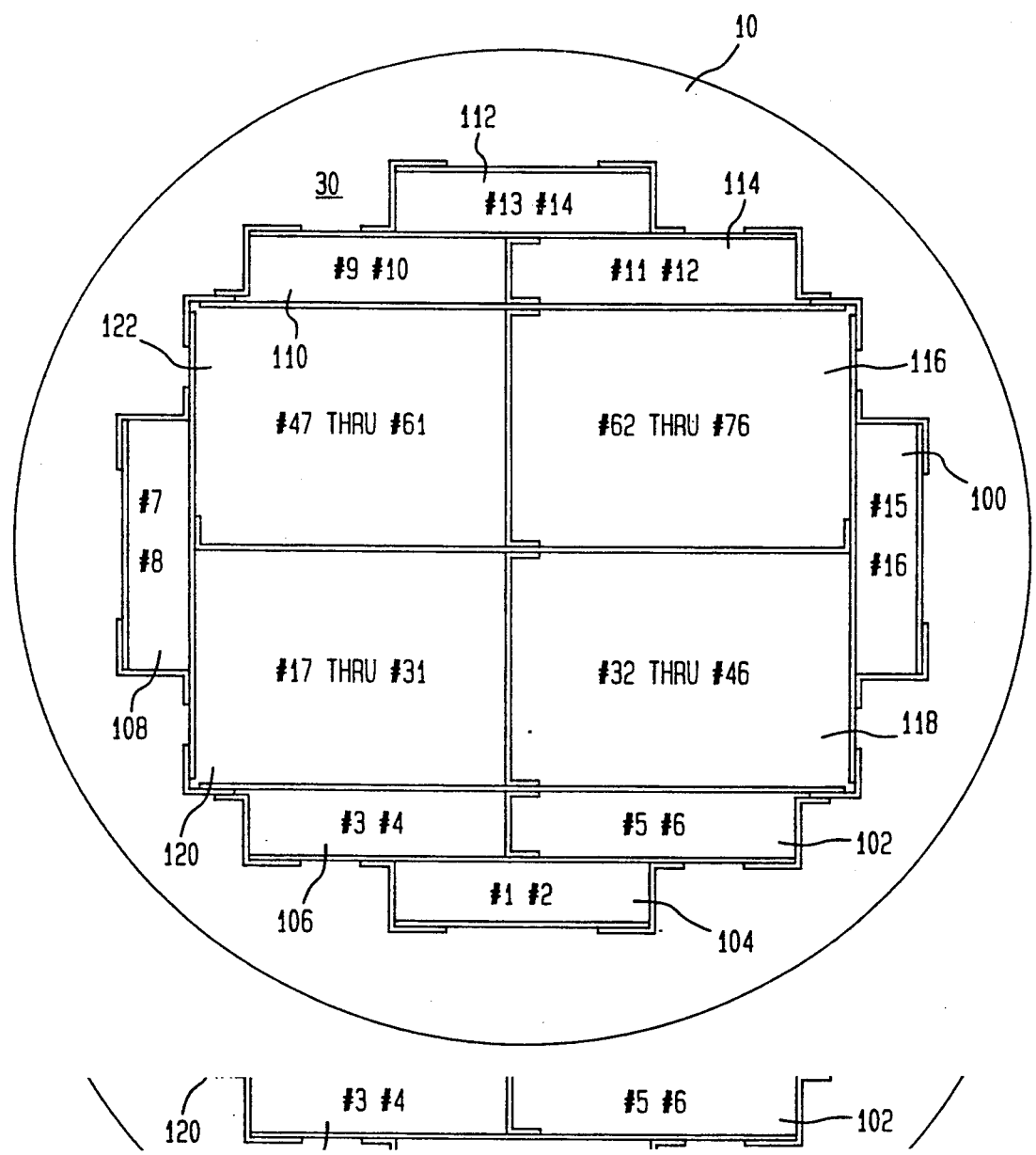

CRYOGENIC STORAGE OF PERISHABLE FLUIDS

BACKGROUND OF THE INVENTION

This invention relates to means and methods of cryogenically storing perishable fluids, and particularly for storing the blood of a donor and accessing the same blood to permit use in behalf of the donor in autogenous blood transfusions.

Cryogenic storage systems conserve perishable commodities such as whole blood, pharmaceuticals, enzymes, semen, living tissues, or other biological specimens by holding them in storage packets arranged in a cryogenic tank at low temperatures for sustained periods. In such systems, removal of a particular blood packet for an autogenous transfusion requires rapid and accurate access to the packet. On the other hand the space in the containers of such systems is precious.

In the part, such systems have been wasteful of space or inefficient in the rapid storage packet. One such system requires removal of many, and in some instances all, of the frozen fluid storage packets out of the cryogenic container to gain access to one packet. Another system requires leaving one sixth of the space in the interior of the cryogenic tank empty to permit shifting a large section of packets into the empty space for subsequent removal of the desired packet. This system requires a complex control arrangement for shifting the packets.

OBJECTS AND SUMMARY OF THE INVENTION

An object of the invention is to overcome these difficulties.

Another object is to improve systems of this type.

Another object is to permit dense packing and easy, efficient access of cryogenically stored fluid packets.

According to a feature of the invention, these and other objects are attained, in whole or in part, by storing the fluid storage packets in an array of individually identified vertically movable racks, each containing a stack of individually identified storage packets, within a grid beneath the opening of a cryogenic tank.

According to another feature of the invention, the storage packets are substantially flat and the racks hold the storage packets in vertical end-to-edge relationship.

These and other features of the invention are pointed out in the claims. Other objects and advantages of the invention will become evident from the following detailed description when read in light of the accompanying drawings.

BRIEF DESCRIPTION OF THE DRAWINGS

FIG. 6 is a front elevation of a rack for holding frozen blood bags or packets.

FIG. 7 is an end elevation of the rack in FIG. 6.

FIG. 12 is a top view of the open tank in FIG. 1 showing the pocket assembly and the racks placed therein.

DETAILED DESCRIPTION OF PREFERRED EMBODIMENTS

Figure 1:
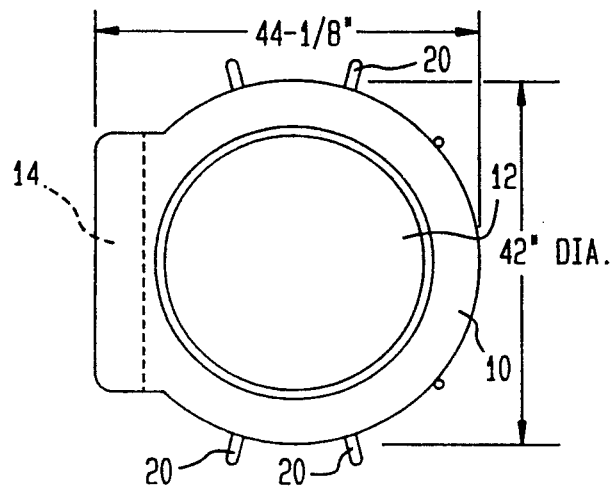
FIG. 1 is an elevation of a tank embodying the invention.
Figure 2:
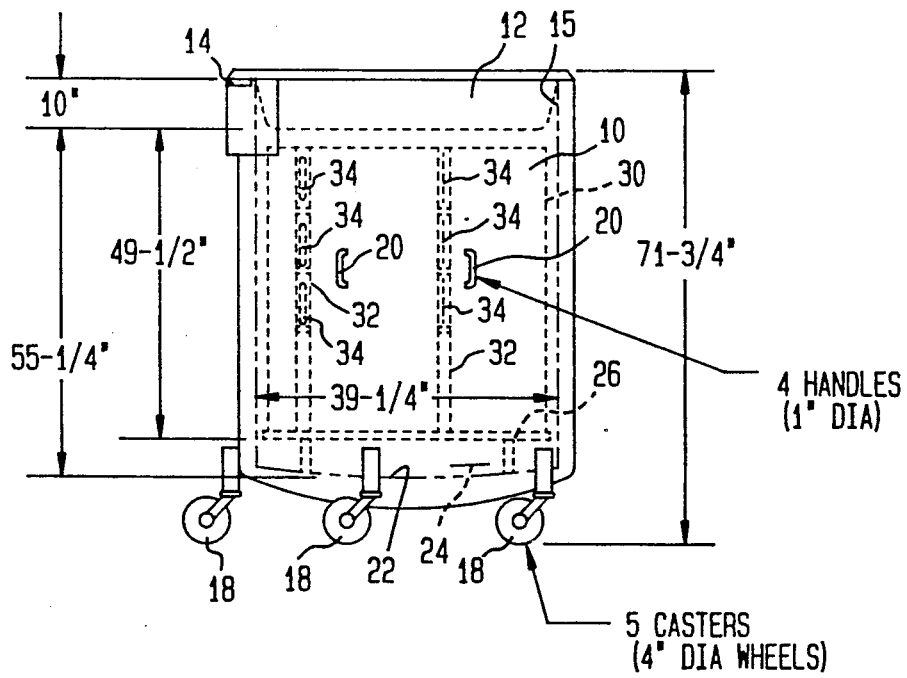
FIG. 2 is a plan view of the tank in FIG.

FIGS. 1 and 2 illustrate a cylindrical tank 10 for cryogenic storage of separated, individually identified, frozen packets of blood preserved for use by the individual donors of the blood. The tank 10 includes a circular lid 12 which a hinge 14 holds for upward articulation to expose an opening 16 at the top of the tank. Five casters 18 and four handles 20 allow for movement of the tank along the floor. A well 22 at the base of the tank 10 holds a supply of liquid nitrogen 24.

A platform 26 with legs holds a pocket assembly or grid 30 within the tank 10. The pocket assembly 30 extends substantially, but just less than, across the entire width of the opening 16 and from the platform 26 virtually up to the lid 12. The pocket assembly 30 appears only schematically in FIGS. 1 and 2. Vertically movable racks 32, also shown only schematically in FIGS. 1 and 2, hold narrow vertically stacked frozen fluid storage packets or bags 34 of blood (also shown schematically).

Figure 5:
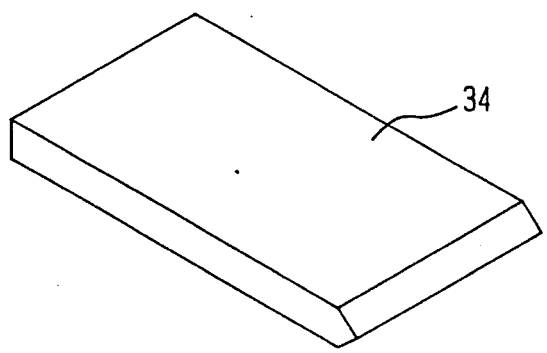
FIG. 5 is a perspective view of a frozen blood bag or packet.
Figure 3:
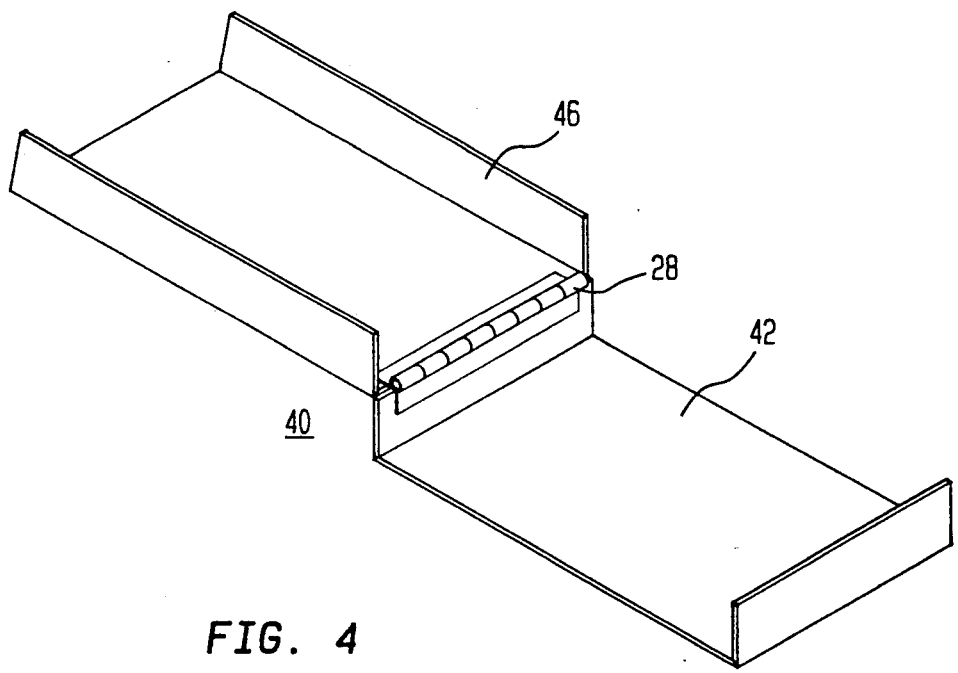
FIG. 3 is a perspective view of a blood bag press for shaping the blood to be frozen.
Figure 4:
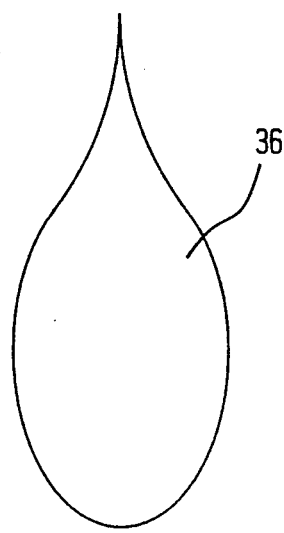
FIG. 4 is an end view of a blood bag before it is frozen.

FIGS. 3, 4 and 5 illustrate the manner of shaping the packet 34 of blood for placement within the racks 32. Here FIG. 4 illustrates a flaccid plastic bag 36 of blood before it is frozen. The blood bag 36 is placed in a rectangular press 40 having a C-shaped base 42 and a C-shaped cover 46 joined by a hinge 48. Placing the filled bag 36 on the base 42 and articulating the cover 46 to close about the plastic bag 34 filled with blood causes the press 40 to shape the filled bag 36 into the rectangular condition shown in FIG. 5. The press 40 is then temporarily placed within the tank 10 or a separate freezer until the blood in the container 36 is frozen into the rectangular shape. This freezing process forms the frozen blood packet or storage packet 34. The blood packet 34 is then removed from the press 40 for placement in the rack 32. The dimensions of the closed press 40, and hence the maximum dimensions of the frozen blood packet 34 are approximately 11" long, 4" wide, and ¾" thick.

Figure 8:
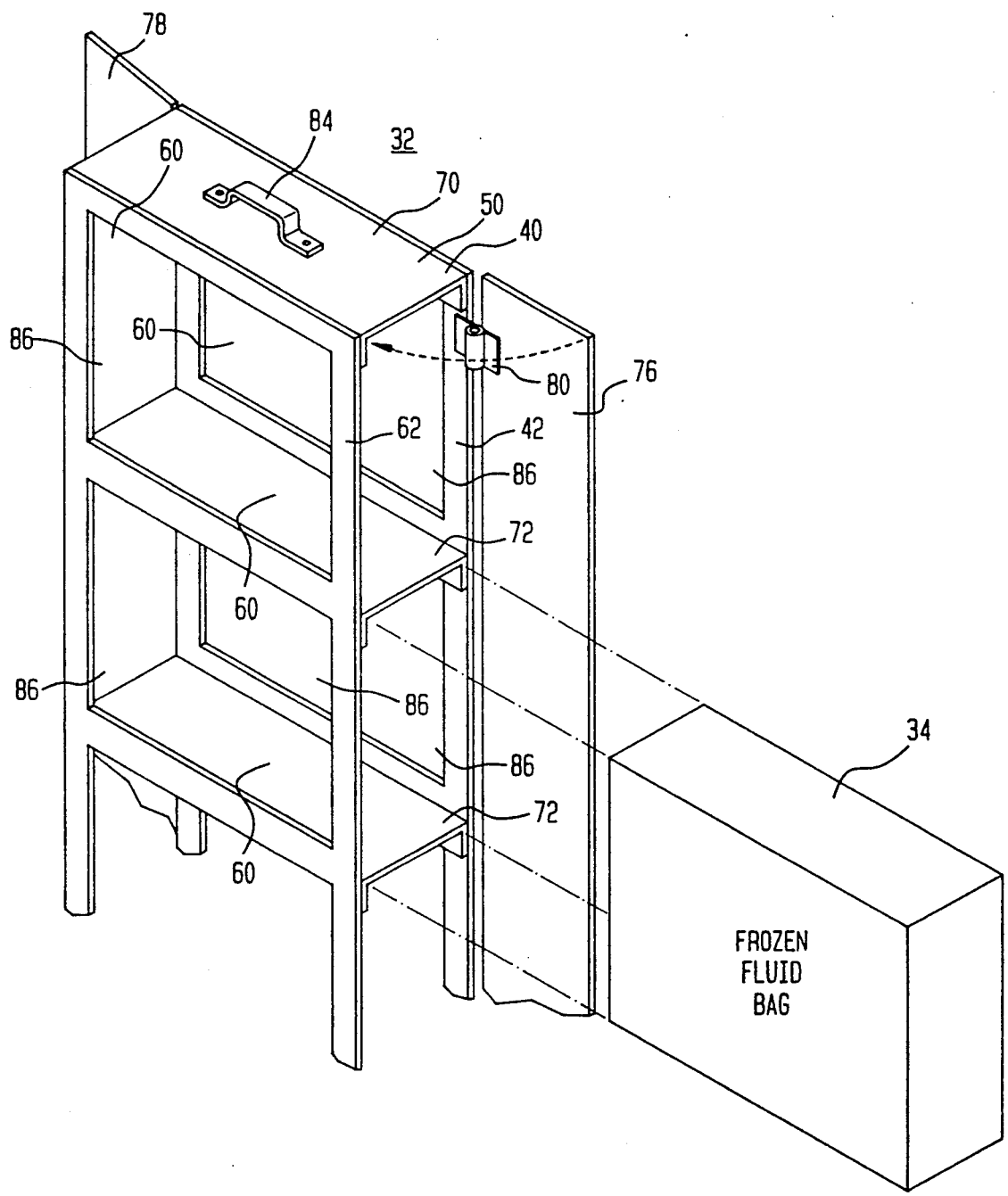
FIG. 8 is a perspective view of the rack in FIGS. 6 and 7.

FIGS. 6, 7, and 8 illustrate one of the racks 32 which holds the frozen blood packets 34 in vertical orientation, (width vertical, thickness and lengths horizontal, in edge-to-edge relationship). Each rack 32 contains open side walls 62, a bottom 64, a top 70, and horizontal shelves 72 to separate the interior of the rack 32 to receive frozen blood packets 34. Hinged doors 76 and 78 held by hinges 80 and appearing at the front and rear narrow ends of the racks 32 retain the frozen blood packets 34 within the racks 32. The doors 76 and 78 at each narrow end open and close to permit insertion and removal of frozen blood packets 34 by sliding them horizontally. A handle 84 at the top 70 allows raising of each rack 32 vertically through the opening 16 at the top of the tank for exposure and insertion or removal of the frozen blood packets 34 through the doors 76 and 78. The side walls 62 have large openings 86 to permit easy flow of cold gases around the frozen blood packets 34.

Figure 9:
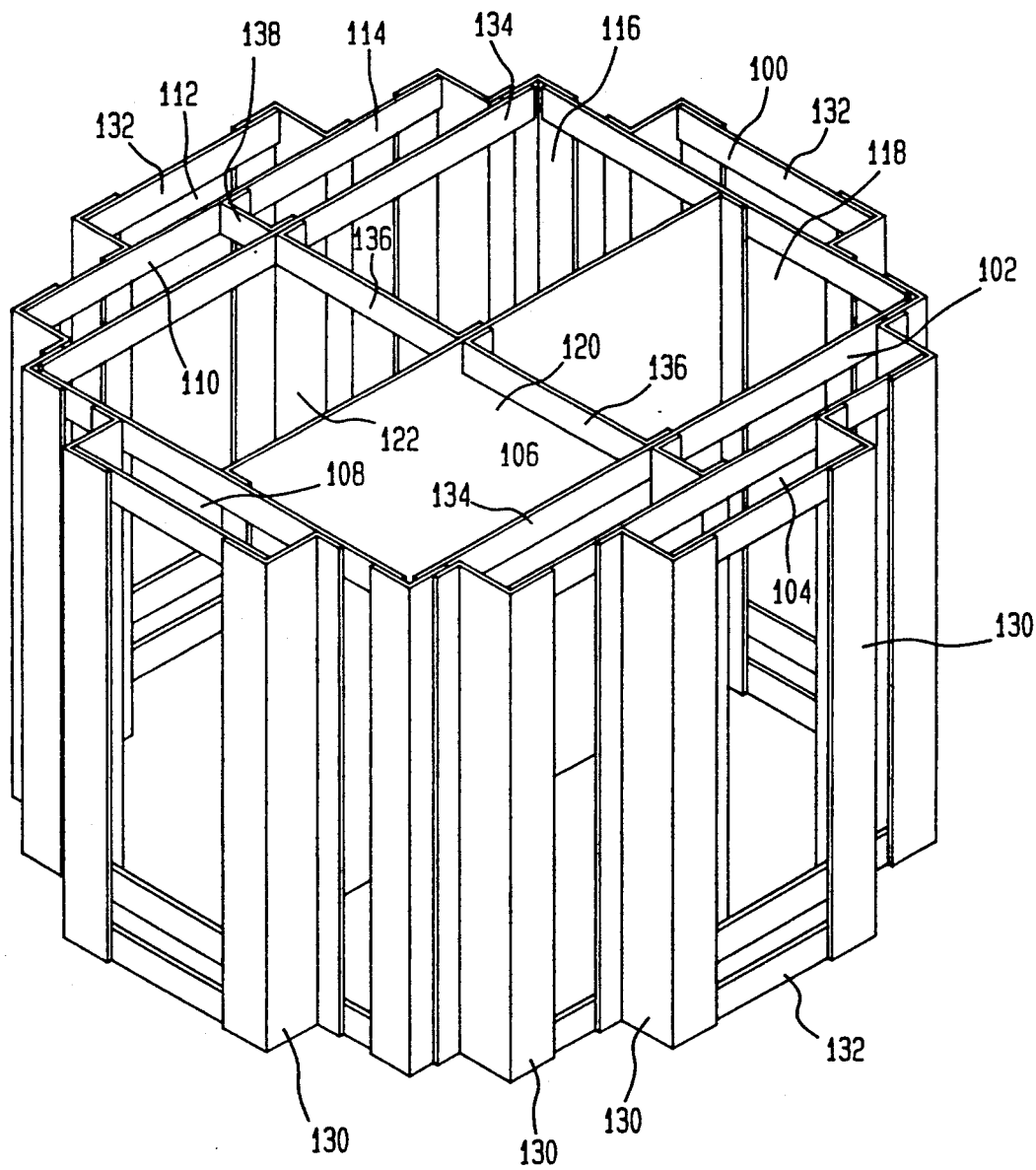
FIG. 9 is a perspective view of a pocket assembly for holding the racks in FIGS. 6, 7 and 8.
Figure 10:
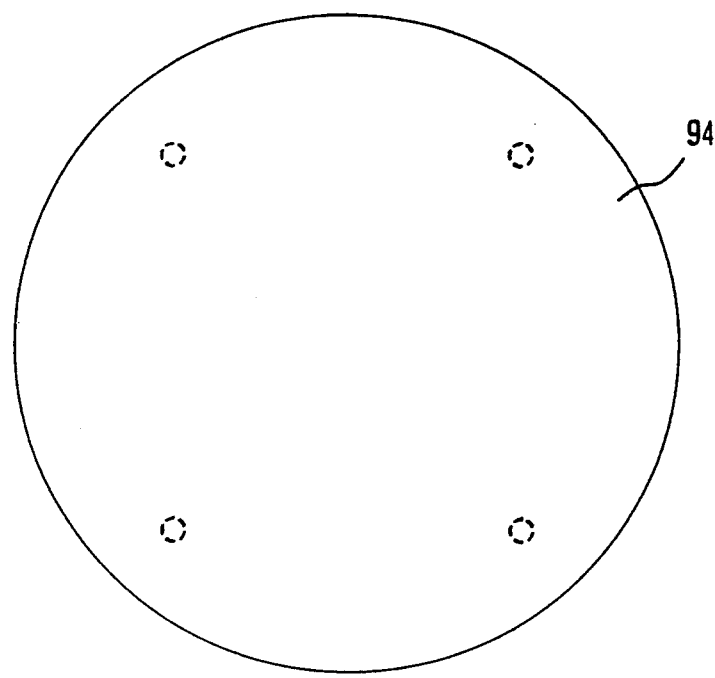
FIG. 10 is a top view of a platform holding the packet assembly of FIG. 9.
Figure 11:
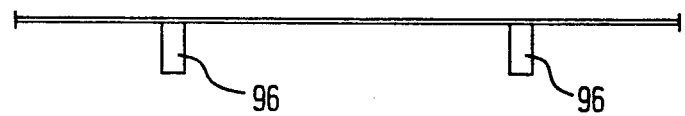
FIG. 11 is side view of the platform in FIG. 10.

The pocket assembly or grid 30 appears in perspective view in FIG. 9. The pocket assembly 30 supports 76 racks 32 in the tank 10. The pocket assembly 30 rests upon the platform 26 which includes a circular horizontal base plate 94. See FIGS. 10 and 11. The horizontal base plate 94 of the platform 26 is made of perforated or expanded metal and has four legs 96 which stand in the supply of liquid nitrogen 24 and lift the plate 94 above the liquid nitrogen.

As shown in FIG. 9, the pocket assembly 30 forms 10 vertical pockets 100 to 122. The pockets 100 to 114 each contain room for two tracks 32 and the 24 racks. The pockets may contain suitable tracks for guiding the vertically removable racks, but such are not necessary. Each of the racks 32 as well as frozen blood packets 34 are identified with a different code so that one can lift any rack out of its compartment and remove any of the frozen blood packets 34 therein.

FIG. 12 illustrates schematically a top view of the pocket assembly 30 within the tank 10. Each pocket carries racks #1 to #72 identified by a particular number. A packet is then identified by its location on the rack 30. This makes rapid access of any packet 34 possible.

In operation, a blood frozen blood packet 34 or blood bag is placed in the press 40 which shapes the filled plastic bags 34 during initial freezing. When the frozen bag 34 is removed from the press 40, a rack 32 is drawn through the opening 16 and a door 76 or 78 swung open to place the frozen blood bag 34 onto a shelf 2 within the rack 32. Each blood bag or packet 34 is identified by a code composed of the pocket number, rack number, and packet number. The codes need not be numerical, but may be alphanumeric.

According to an embodiment of the invention, a chain and pulley arrangement is mounted above the tank 10 so that one end of the chain can hook into the handle 84 atop any rack 32 to hoist any rack for loading and unloading.

The system of the invention allows dense packing of frozen fluid frozen blood packets such as frozen blood frozen blood packets and yet easy removal of only one vertical rack 42 to access any one of the frozen blood packets 34.

To form the pocket assembly 30, suitable welds join Z-angles 130, strip braces 132 and 134, C-braces 136, and C-angles 138.

According to the invention, the packets 34 may contain frozen fluids other than blood. It is well known that different biological compounds may require different storage temperatures. The dense packing of the packets 34 according to the invention may be used with other means to cut down the gas flow and create different temperature zones. The disparate levels may be used for fluids with dissimilar temperature needs. According to another feature of the invention, the gas flow is maintained to create substantially equal temperatures throughout the tank.

The system of the invention affords dense packing and easy access to individually identified storage packets 34 of frozen fluid, such as blood. The grid 30 forms the racks 32 into an array which is individually identified and vertically movable. Each rack 32 contains a stack of individually identified storage packets and is located within the grid 30 beneath the opening 16 of the cryogenic tank 10. The storage packets 34 are substantially flat and the racks 32 hold the storage packets in vertical edge-to-edge relationship.

While embodiments of the invention have been described in detail, it will be evidence of those skilled in the art that the invention may be embodied otherwise without departing from its spirit and scope.

What is claimed is:

1. A storage system, comprising:
   a tank for holding liquid gas for producing cryogenic temperatures within the tank, said tank having an opening at the top;
   random access holding means for holding a plurality of frozen packets within said tank in such a manner as to be randomly accessible;
   said random access means including a plurality of vertical shaped racks each having a plurality of overlying horizontal shelves for holding said packets;
   said random access holding means including a grid supported in said tank for receiving said racks and holding all of said racks below the opening and for allowing vertical movement of single ones said racks relative to said grid and through the opening.

2. A system as in claim 1, wherein said racks have a long dimension extending vertically, and a horizontally arranged narrow dimension, said rack having an opening along the narrow dimension for receiving a plurality of narrow packets and arranging them in vertical edge-to-edge relationship.

3. A system as in claim 1, wherein said opening in said tank extends substantially over the entire width of the tank.

4. A system as in claim 1, wherein said opening in said tank extends substantially over the entire width of the tank and said grid has a width substantially equal to but slightly smaller than said opening.

5. A system as in claim 1, wherein said grid forms a plurality of vertical pockets each for slidably receiving at least one of said racks.

6. A system as in claim 1, wherein said grid forms a plurality of vertical pockets each for slidably receiving at least one of said racks; a plurality of said vertical pockets each being arranged to receive a plurality of racks.

7. A system as in claim 1, wherein said grid forms a plurality of vertical pockets each for slidably receiving at least one of said racks, said pockets each having open sidewalls for holding said racks and for permitting flow of gases into the packets within the racks.

8. A system as in claim 1, wherein said racks each have sidewalls for holding the packets, a plurality of said sidewalls each having an opening for permitting flow of cold gases.

9. A system as in claim 1, wherein said racks are each vertically elongated, each of said shelves dividing the racks across the direction of elongation and receiving a packet on said shelves.

10. A system as in claim 1, wherein said racks are each vertically elongated, each of said shelves dividing the racks across the direction of elongation and receiving a packet on said shelves, said racks having a horizontal longer dimension and a horizontal narrow dimension, said shelves being spaced a distance less that the horizontal longer dimension.

* * * * *